US009161738B2

(12) United States Patent
Tsung

(10) Patent No.: US 9,161,738 B2
(45) Date of Patent: Oct. 20, 2015

(54) ULTRASONIC PROBE DEVICE AND SYSTEM AND METHODS OF GENERATING ULTRASONIC IMAGES

(75) Inventor: James W. Tsung, New York, NY (US)

(73) Assignee: New York University, New York, NY (US)

(*) Notice: Subject to any disclaimer, the term of this patent is extended or adjusted under 35 U.S.C. 154(b) by 657 days.

(21) Appl. No.: 12/692,400

(22) Filed: Jan. 22, 2010

(65) Prior Publication Data

US 2010/0191123 A1 Jul. 29, 2010

Related U.S. Application Data

(60) Provisional application No. 61/147,236, filed on Jan. 26, 2009.

(51) Int. Cl.
*A61B 8/00* (2006.01)
*A61B 8/12* (2006.01)
(52) U.S. Cl.
CPC .. *A61B 8/12* (2013.01); *A61B 8/445* (2013.01)
(58) Field of Classification Search
CPC .... A61B 8/12; A61B 8/4461; A61B 10/0291; A61B 2019/5276; A61B 1/31
USPC ................................................ 600/437–461
See application file for complete search history.

(56) References Cited

U.S. PATENT DOCUMENTS

| 5,090,414 | A | | 2/1992 | Takano | |
|---|---|---|---|---|---|
| 5,546,948 | A | * | 8/1996 | Hamm et al. | 600/585 |
| 5,810,007 | A | * | 9/1998 | Holupka et al. | 600/439 |
| 5,931,788 | A | * | 8/1999 | Keen et al. | 600/462 |
| 7,115,093 | B2 | * | 10/2006 | Halmann et al. | 600/437 |
| 2003/0195426 | A1 | | 10/2003 | White et al. | |
| 2005/0051597 | A1 | | 3/2005 | Toledano | |
| 2007/0088213 | A1 | * | 4/2007 | Poland | 600/437 |
| 2008/0146936 | A1 | | 6/2008 | Furia et al. | |

FOREIGN PATENT DOCUMENTS

WO 2008091938 A1 7/2008

* cited by examiner

*Primary Examiner* — Elmer Chao
(74) *Attorney, Agent, or Firm* — LeClairRyan, a Professional Corporation

(57) ABSTRACT

The present invention relates to an ultrasonic probe device comprising an elongated body having a proximal end and a distal end, where the body has a channel that extends from the proximal end to the distal end. A cord passes through the channel and is extendable and retractable relative to the distal end of the elongated body. An ultrasonic probe head is connected to the cord and has a proximal end adjacent the distal end of the elongated body. The proximal end of the probe head is detachably connected to the distal end of the elongated body. The present invention is also directed to an ultrasound imaging system and a method of generating an ultrasonic image.

16 Claims, 5 Drawing Sheets

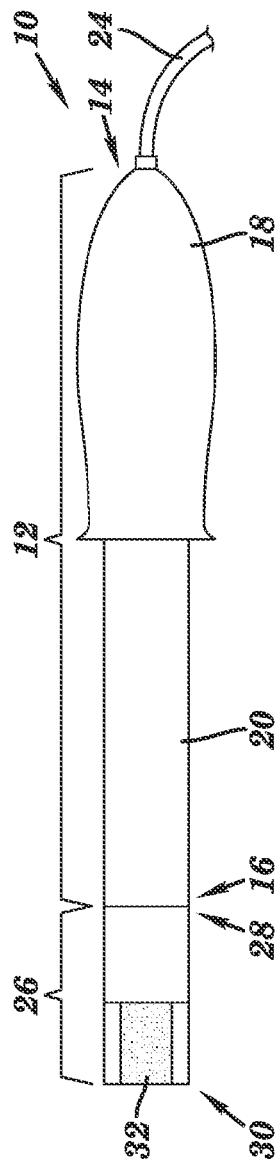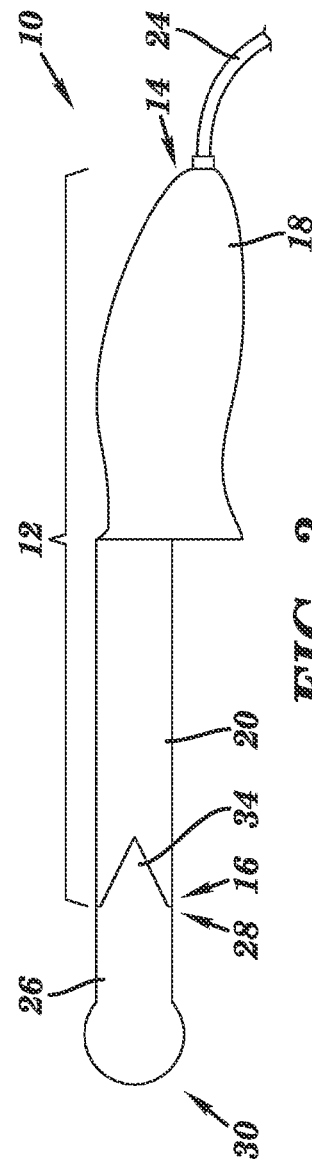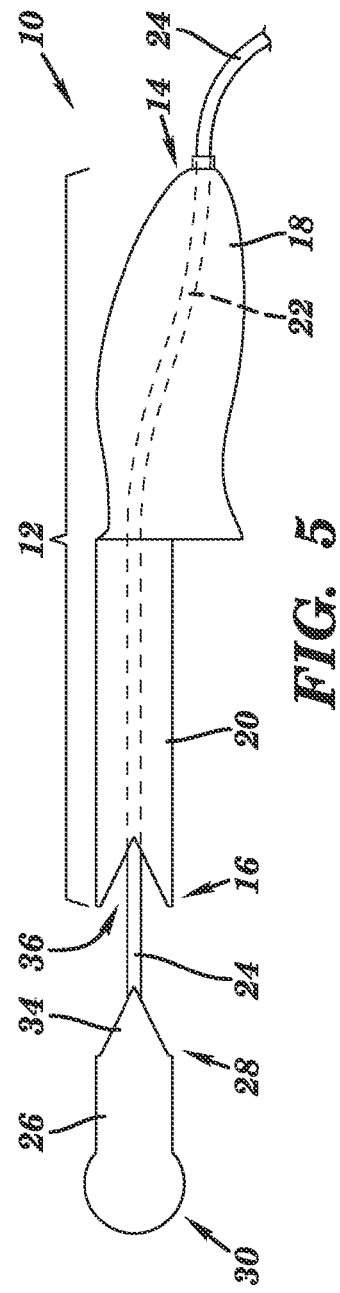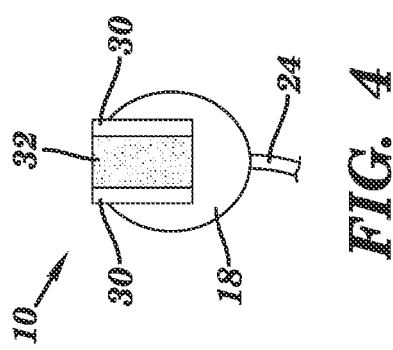

ULTRASONIC PROBE DEVICE AND SYSTEM AND METHODS OF GENERATING ULTRASONIC IMAGES

This application claims the priority benefit of U.S. Provisional Patent Application Ser. No. 61/147,236, filed Jan. 26, 2009, which is hereby incorporated by reference in its entirety.

FIELD OF THE INVENTION

The present invention relates to ultrasonic probe devices and systems and methods of generating ultrasonic images.

BACKGROUND OF THE INVENTION

Point-of-care ultrasound use has expanded in many fields of medicine, particularly emergency medicine, for the past two decades and more recently in pediatrics for the last decade as more compact, portable, and relatively inexpensive ultrasound machines have come to market. Given the endless range of diagnostic problems clinicians encounter in the emergency department, a wide variety of ultrasound probes may be needed depending on the diagnostic problem. These include transvaginal/intracavitary probes for the evaluation of vaginal bleeding and suspected ectopic pregnancy; phased array cardiac probes for the evaluation of pericardial effusion, left ventricular function, and cardiac arrest; curved abdominal probes for the evaluation of intraperitoneal bleeding from trauma, abdominal aortic aneurysms, or acute cholecystitis; linear transducers for soft tissue/musculoskeletal disorders, and procedural guidance, such as central line placement; and tightly curved array microconvex probes for pediatric/neonatal applications, regional nerve blocks, and other procedures.

The maximum number of ultrasound probes that can be connected to console-type or cart-based ultrasound machines currently on the market is three. This poses problems for clinicians who may switch among more than three different probes depending on the diagnostic problem or ultrasound guided procedure needed to be performed. Newer handheld ultrasound machines are marketed with a single non-detachable probe (often a phased array probe commonly used for cardiac imaging), which also limits functionality of these types of ultrasound machines. Furthermore, in environments such as emergency departments and intensive care units where space and storage are often in short supply, extra probes not connected to an ultrasound machine may be lost or stolen.

The present invention is directed to overcoming these and other deficiencies in the art.

SUMMARY OF THE INVENTION

One aspect of the present invention is directed to an ultrasonic probe device having an elongated body with a proximal end and a distal end. The body has a channel that extends from the proximal end to the distal end. A cord passes through the channel and is extendable and retractable relative to the distal end of the elongated body. The probe device also has an ultrasonic probe head connected to the cord and having a proximal end adjacent the distal end of the elongated body. The proximal end of the probe head is detachably connected to the distal end of the elongated body.

Another aspect of the present invention is directed to an ultrasound imaging system. This system includes a central processing unit and a display operably connected to the central processing unit. The display shows processed data from the central processing unit. The ultrasound imaging system also includes an ultrasonic probe device of the present invention operably connected to the central processing unit by the cord to send and receive sound waves to/from the central processing unit.

A further aspect of the present invention is directed to a method of generating an ultrasonic image. This method involves providing an ultrasound imaging system according to the present invention and inserting the probe head into a subject or scanning the surface of a subject's body with the probe head under conditions effective to generate an ultrasonic image.

The present invention enables the performance of a broad range of ultrasound applications and procedures with a single probe device by enabling one probe to have the functionality of at least two probes. For example, the ultrasonic probe device of the present invention can be used as an intracavitary probe for use in e.g., OB/GYN applications and a tightly curved array probe for use in e.g., pediatric/procedural applications. The invention and design would also apply to 4D (3D plus real-time) intracavitary probe technology, more commonly used in the field of reproductive endocrinology. Accordingly, the ultrasonic probe device of the present invention permits an increase in the functionality of probe devices that connect to current ultrasound systems by adding a two-in-one probe feature.

BRIEF DESCRIPTION OF THE DRAWINGS

As shown in FIG. 1, the probe head is detached from the distal end of the elongated body.

FIG. 2 is a top view of one embodiment of the ultrasonic probe device of the present invention where the probe head is connected at its proximal end to the distal end of the elongated body. The probe head has a convex surface at its distal end and includes a transducer element on the convex surface.

FIG. 3 is a side view of one embodiment of the ultrasonic probe device of the present invention where the probe head is connected at its proximal end to the distal end of the elongated body. As shown, the probe head has a convex surface at its distal end.

FIG. 4 is a front view of one embodiment of the ultrasonic probe device of the present invention where the probe head is connected at its proximal end to the distal end of the elongated body. A transducer element on the convex surface of the distal end of the probe head can be seen.

FIG. 5 is a side view of one embodiment of the ultrasonic probe device of the present invention where the probe head is detached from the distal end of the elongated body. The probe head is shown to have a convex surface at its distal end. Also shown is a channel that extends from the proximal end to the distal end of the elongated body and a cord that passes through the channel.

DETAILED DESCRIPTION OF THE INVENTION

The present invention is directed to ultrasonic probe devices, ultrasound imaging systems that include the ultrasonic probe devices, and methods of generating ultrasonic images.

Figure 1:
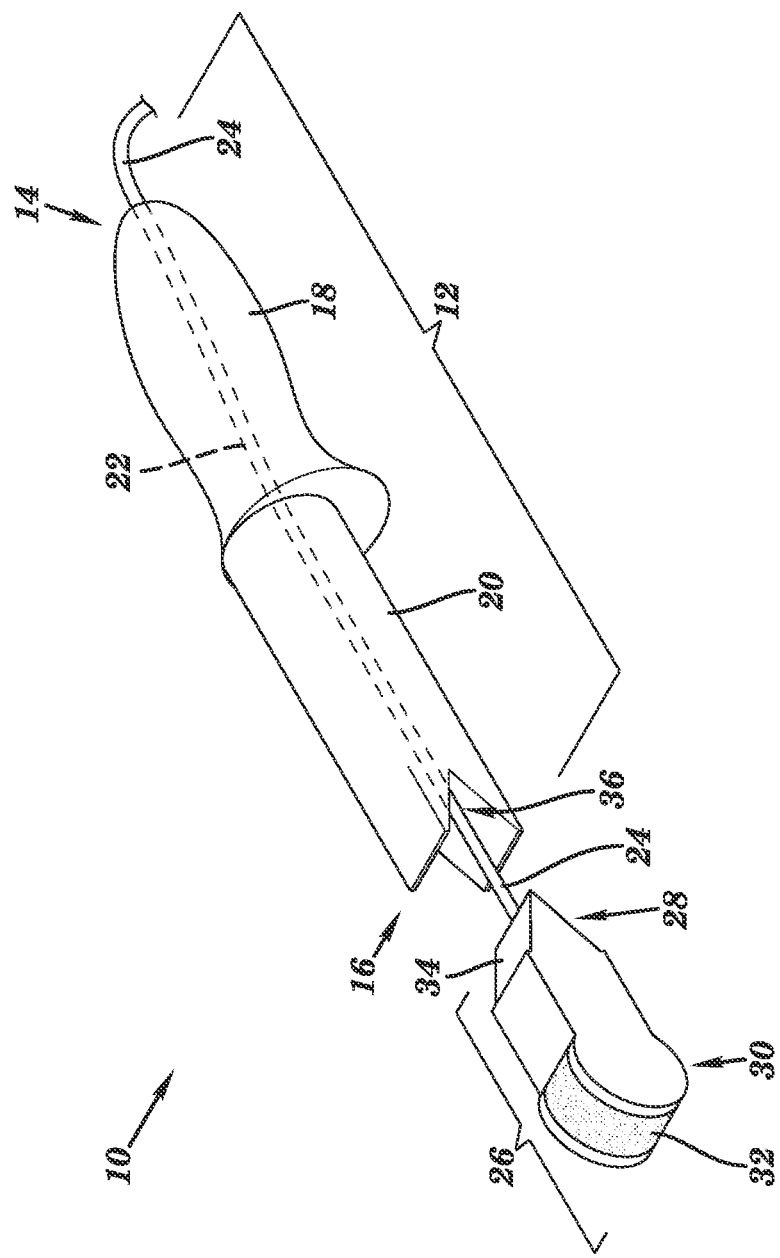
FIG. 1 is a perspective view of one embodiment of the ultrasonic probe device of the present invention. The ultrasonic probe device has an elongated body having a proximal end and a distal end and a channel that extends from the proximal end to the distal end. A cord passes through the channel and is extendable and retractable relative to the distal end of the elongated body. An ultrasonic probe head is connected to the cord and has a proximal end adjacent the distal end of the elongated body.

An ultrasonic probe device according to one embodiment of the present invention is shown in FIG. 1. As illustrated, ultrasonic probe device 10 has elongated body 12 with proximal end 14 and distal end 16. Elongated body 12 includes handle 18 at proximal end 14 and cylindrically-shaped shaft 20 at distal end 16. Channel 22 resides in elongated body 12 and extends from proximal end 14 to distal end 16 of elongated body 12. Cord 24 passes through channel 22 and is extendable and retractable relative to at least distal end 16 of elongated body 12.

Ultrasonic probe device 10 also includes probe head 26, which is connected to cord 24 at proximal end 28. Probe head 26 includes distal end 30 which, in the embodiment illustrated in FIG. 1, has a convex shape. Transducer element 32 is located at distal end 30 of probe head 26. Transducer element 32 at distal end 30 of probe head 26 may image in 4D/3D (e.g., matrix array) or conventional 2D B-mode imaging. Proximal end 28 of probe head 26 is positioned adjacent distal end 16 of elongated body 12, and may be detachably connected to distal end 16. In the particular embodiments illustrated in FIGS. 1 and 5-10, probe head 26 is detached from shaft 20. In contrast, FIGS. 2, 3, and 4 show an embodiment of ultrasonic probe device 10 where probe head 26 is attached (or positioned directly adjacent) to distal end 16 of shaft 20.

Attachment of probe head 26 to distal end 16 of elongated body 12 may involve a coupling, as illustrated in FIG. 1 by wedge 34 of proximal end 28 of probe head 26, which fits into socket 36 of shaft 20. As shown in the particular embodiment of FIG. 1, socket 36 and wedge 34 fit together and operate to prevent elongated body 12 from rotating relative to probe head 26. Locking joints for detachably connecting probe head 26 to distal end 16 are discussed infra.

Elongated body 12 of the ultrasonic probe device of the present invention may be configured to include shaft 20 at proximal end 16 and handle 18 at proximal end 14, as shown in FIG. 1. When employed, handle 18 is provided as a means for assisting a clinician's control of the ultrasonic probe device in various imaging scenarios, including different relative positions of the clinician and a patient, and varying patient conditions. Also, a range of gripping styles and hand sizes can be accommodated at handle 18 beyond what is illustrated in FIG. 1. In considering particular designs, handle 18 should be comfortable to hold and easily controllable with minimal gripping force to reduce fatigue and the occurrence of occupational injury. As can be seen in FIGS. 3 and 5-10, handle 18 may be in a slightly off-set position relative to shaft 20 of elongated body 12. However, elongated body 12 (including handle 18 and/or shaft 20) is not limited to the particular designs and features illustrated, and may include other designs and features depending on the particular use of the probe device, as discussed in more detail infra. One particular variation from the illustrated probe device may include a longer/shorter or broader/narrower shaft 20. The particular length and width of shaft 20 will depend on the particular intracavitary imaging procedures being carried out with the ultrasonic probe device.

Elongated body 12 and probe head 26 may be constructed of a variety of materials commonly known and used in intracavitary (e.g., transvaginal) ultrasonic probe devices. Typically, intracavitary ultrasonic probe devices have a rigid construction and are fabricated from hard plastic materials. The ultrasonic probe device of the present invention is not limited to any particular material of fabrication.

Channel 22 of elongated body 12 may have a width larger than the diameter of cord 24, thereby permitting elongated body 12 to be moved along cord 24 toward or away from proximal end 28 of probe head 26. As described in more detail infra, the ability to move elongated body 12 away from probe head 26 or toward and detachably connected to probe head 26 permits a clinician to use the probe device of the present invention in a variety of procedures. It may be desirable to include on elongated body 12 a mechanism by which elongated body 12 may be held at a particular position along cord 24 either away from or adjacent to probe head 26.

Probe head 26 may be of a variety of designs and/or sizes commonly used in ultrasonic imaging. Various types of probe heads are known and used in ultrasonic imaging, including convex, sector, linear, and oblique shaped probe heads. Curved (e.g., convex) probe heads with a plurality of electroacoustic transducer elements disposed along an arc are described in U.S. Pat. No. 4,281,550, to Erikson, which is hereby incorporated by reference in its entirety. A particularly suitable design for a probe head of the ultrasonic probe device of the present invention is a design that would accommodate use of the probe head in ultrasonic imaging procedures both with a probe device body (e.g., elongated body 12) and independent of a probe device body. As described in more detail infra, probe device 10 illustrated in FIG. 1 is an example of a probe device having a probe head (i.e., probe head 26) that can accommodate imaging procedures with or without attachment to elongated body 12. In this particular embodiment, probe head 26 has a design that permits its use in ultrasonic imaging procedures either together with or separate from elongated body 12.

Transducer element 32 located on probe head 26 may be in the form of any typical transducer element known and used in ultrasound imaging probes. An ultrasonic transducer typically includes a plurality of transducer elements which are arranged along a scan direction. The transducer elements vibrate and generate the ultrasound pulses which are transmitted to a patient's body. The transducer elements also receive the echo signals from the body. According to one embodiment, transducer element 32 is divided into a plurality of piezo-electric ceramic elements, each emitting ultrasound waves in a plane perpendicular to the surface of transducer element 32 to perform sector scanning electronically. Each piezo-electric ceramic element may have an elongated rectangular shape provided such that the longer sides are adjacent to one another, as described in U.S. Pat. No. 5,469,852 to Nakamura et al., which is hereby incorporated by reference in its entirety. Ultrasonic transducers are also described in U.S. Pat. No. 4,281,550, which is hereby incorporated by reference in its entirety. Thus, for example, by rotating probe head 26, a scanning plane of the ultrasound wave rotates to obtain cross-sectional images along various angles without changing the direction of probe head 26. Other known or yet to be discovered transducer elements and/or designs thereof may also be employed.

Cord 24 is, in a particular embodiment, a power cord capable of delivering power to probe head 26 to enable transducer element 32 to send and receive ultrasound signals. Cord 24 may be any length. A typical cord length for attaching an ultrasound probe device to an ultrasound machine is about 4-6 feet, but may be longer or shorter depending on the specific design of the ultrasound machine being used and the type of procedure being carried out. In one embodiment, cord 24 may be several feet in length but is a retractable cord that is wound in a housing positioned e.g., at or near the ultrasound machine. The retractable cord housing may be designed with a locking mechanism whereby the clinician can extend the cord from the housing to a desired length which length can then be maintained by the locking mechanism until the locking mechanism is released and the cord is then retracted back into the housing. By this means, the clinician can select the desired length of the cord according to the type of procedure being carried out and/or the relative position of the clinician and/or patient to the ultrasound machine to which the ultrasound probe is connected.

As mentioned supra, probe head 26 is detachably connected to shaft 20. Connection of probe head 26 to distal end 16 of shaft 20 may be carried out, for example, by moving probe head 26 toward distal end 16 of elongated body 12 as elongated body 12 is moved along cord 24 toward proximal end 28 of probe head 26. A mechanism at or near proximal end 14 of elongated body 12 may be employed to prevent elongated body 12 from becoming disconnected from probe head 26. Suitable mechanisms may include, for example, a clip, clamp, or cord fastener such as that described in PCT Patent Publication No. WO 88/02077, which is hereby incorporated by reference in its entirety. It may be desirable to have the mechanism incorporated into elongated body 12.

Alternatively (or, in addition), a locking joint located at proximal end 28 of probe head 26 and/or distal end 16 of shaft 20 may be employed to secure probe head 26 to elongated body 12. Suitable locking joints may include a magnetic lock, a Luer Lock, a modified Luer Lock, a twist lock, a screw lock, or a releasable grip lock. Other types and designs of locking joints may also be used so long as they provide for stable attachment and immediate release of probe head 26 to/from elongated body 12.

One suitable locking joint mechanism may involve magnetic attraction. By way of example, wedge 34 and socket 36 as illustrated in FIG. 1 could be constructed so as to have magnetic attraction that keeps probe head 26 in contact with elongated body 12. According to this embodiment, probe head 26 is held connected to elongated body 12 by magnets positioned in each of wedge 34 and socket 36. These magnets cause an attractive force between wedge 34 and socket 36. Probe head 26 can be easily disconnected from elongated body 12 by simply forcing probe head 26 away from elongated body 12.

Figure 6:
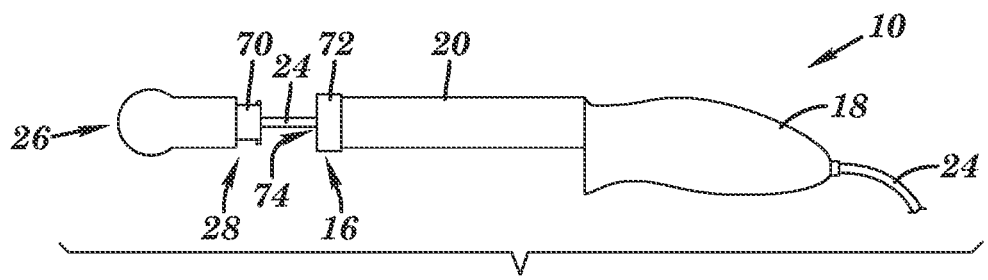
FIG. 6 is a side view of one embodiment of the ultrasonic probe device of the present invention where the probe head is connectable to the elongated body by a Luer Lock mechanism. The Luer Lock mechanism may take shapes other than a circle, such as oval, square, or rectangle to prevent the probe head from rotating when attached to the proximal elongated probe handle.

Another suitable locking joint of the present invention is a Luer Lock type mechanism, as illustrated in FIG. 6. As illustrated, male nose portion 70 is adapted to fit within female receiver 74. These two pieces are locked together with threaded hub engagement 72. This type of locking joint is easily connected by inserting male nose portion 70 into female receiver 74 and then twisting hub engagement 72. Likewise, this locking joint can be released by twisting hub engagement 72 and pulling probe head 26 away from shaft 20. In one embodiment, male nose portion 70 may be tapered to fit tightly into a correspondingly tapered female receiver 74. Variations on Luer Lock connectors are well known, some of which are discussed in U.S. Pat. No. 5,620,427 to Werschmidt et al., which is hereby incorporated by reference in its entirety.

Figure 7:
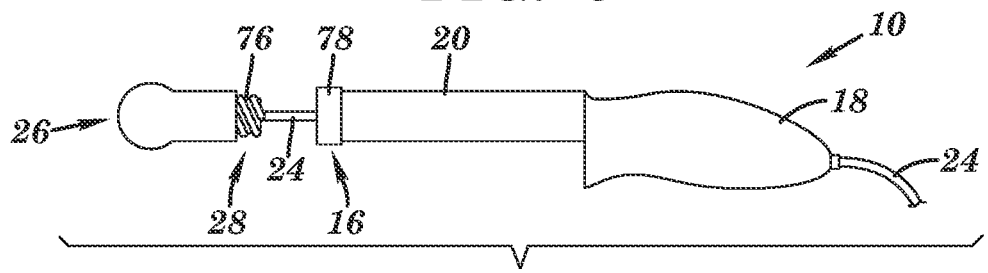
FIG. 7 is a side view of one embodiment of the ultrasonic probe device of the present invention where the probe head is connectable to the elongated body by a twist lock mechanism.

A further suitable locking joint for releasably connecting probe head 26 to shaft 20 is a twist lock, as illustrated in FIG. 7. As illustrated, connector house 78 is located at distal end 16 of shaft 20 and locking collar 76 is located at proximal end 28 of probe head 26. Connecting probe head 26 to shaft 20 according to this embodiment can be carried out by bringing locking collar 76 adjacent connector house 78 and twisting probe head 26 or shaft 20 relative to one another. Shaft 20 and probe head 26 can then be disconnected by twisting and then pulling elongated body 12 away from probe head 26 along cord 24. The basic structure of a twist lock is discussed in further detail in U.S. Pat. No. 6,634,897 to Cykon et al., which is hereby incorporated by reference in its entirety.

Figure 8:
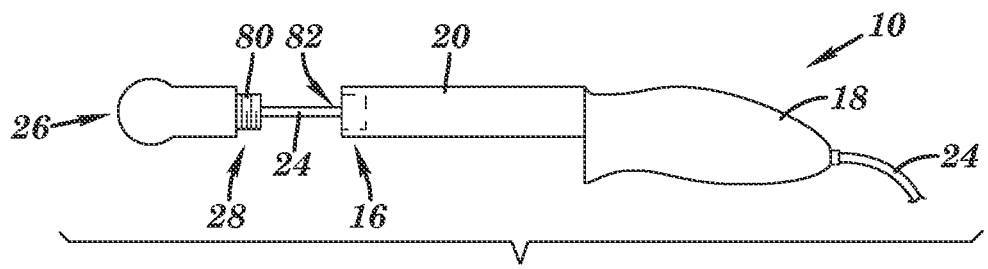
FIG. 8 is a side view of one embodiment of the ultrasonic probe device of the present invention where the probe head is connectable to the elongated body by a screw lock mechanism. According to the embodiment illustrated, the elongated body has at its distal end an interior threading which mates with the coupling screw at the proximal end of the probe head.
Figure 9:
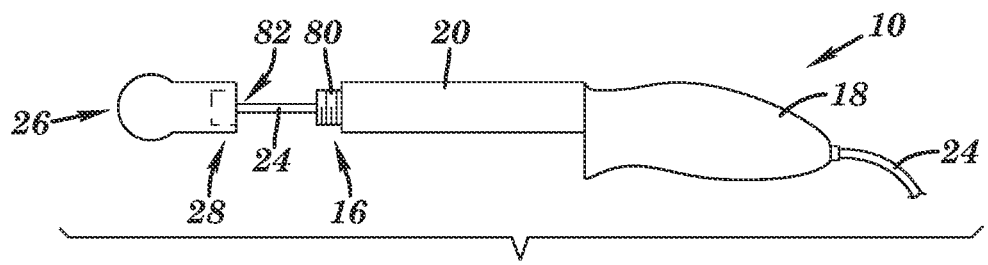
FIG. 9 is a side view of one embodiment of the ultrasonic probe device of the present invention where the probe head is connectable to the elongated body by a screw lock mechanism. According to the embodiment illustrated, the probe head has at its proximal end an interior threading which mates with the coupling screw at the distal end of the elongated body.

Yet another embodiment of the locking joint is a screw lock, as illustrated in FIGS. 8 and 9. According to the embodiment illustrated in FIG. 8, distal end 16 of shaft 20 has interior threading 82 with which coupling screw 80, located at proximal end 28 of probe head 26, is mated. According to the embodiment illustrated in FIG. 9, proximal end 28 of probe head 26 has interior threading 82 with which coupling screw 80, located at distal end 16 of elongated body 12, is mated. Connecting and disconnecting probe head 26 to/from elongated body 12 can be carried out similar to connection and disconnection with a twist lock as described above, except that a screw lock is typically fitted with more threads than a twist lock.

Figure 10:
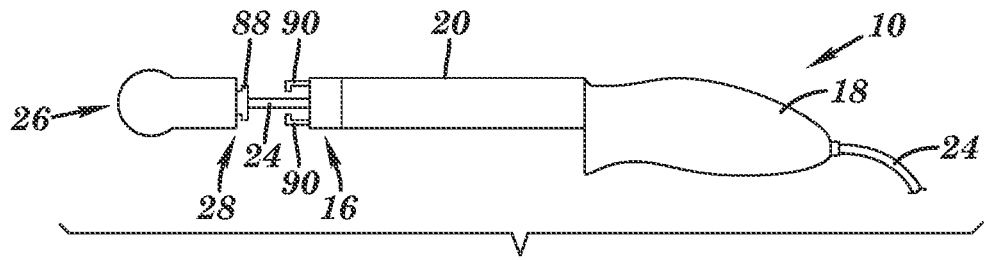
FIG. 10 is a side view of one embodiment of the ultrasonic probe device of the present invention where the probe head is connectable to the elongated body by a grip lock mechanism.

Still another suitable locking joint is a releasable grip lock, as generally illustrated in FIG. 10. As illustrated, fingers 90 protruding from distal end 16 of shaft 20 are connectable to and grip locking mechanism 88 located at proximal end 28 of probe head 26 when probe head 26 is brought adjacent distal end 16 of shaft 20. A means whereby fingers 90 can be spaced apart while being connected to or disconnected from locking mechanism 88 may be incorporated into elongated body 12.

In yet another embodiment, probe head 26 may be held connected to elongated body 12 by cord 24 (or another separate cord). According to this embodiment, cord 24 (or another separate cord) may be e.g., a shock cord capable of applying tension to probe head 26 to keep it connected to elongated body 12. In yet another embodiment, probe head 26 may be held together with elongated body 12 by a locking joint on the exterior surface of elongated body 12 and probe head 26.

The ultrasonic probe device of the present invention may also include a needle assembly detachably or permanently mounted to the probe device for obtaining tissue and fluid samples or administering guided regional anesthesia. The assembly would preferably include a needle and an elongated guide for receiving and guiding the needle. An exemplary needle assembly is described in U.S. Pat. No. 4,742,829 to Law et al., which is hereby incorporated by reference in its entirety.

The ultrasonic probe device of the present invention is used to obtain ultrasonic images of tissue and/or organs during e.g., medical procedures or examinations. Typically, the ultrasonic probe device is used in conjunction with a larger ultrasound imaging system, whereby images are generated and displayed for analysis by a clinician. Accordingly, another aspect of the present invention is directed to an ultrasound imaging system. This system includes a central processing unit and a display operably connected to the central processing unit. The display shows processed data from the central processing unit. The ultrasound imaging system also includes an ultrasonic probe device of the present invention operably connected to the central processing unit by the cord (e.g., an electrical cord) to send and receive sound waves to/from the central processing unit.

Ultrasound systems are well-known in the art and are described, for example, in U.S. Pat. No. 5,758,649 to Iwashita et al.; U.S. Pat. No. 5,839,442 to Chiang et al; U.S. Pat. No. 5,795,297 to Daigle; U.S. Pat. No. 6,558,326 to Pelissier; U.S. Pat. No. 7,066,881 to Song et al.; and U.S. Pat. No. 7,367,945 to Dasgupta et al.; all of which are hereby incorporated by reference in their entirety.

Figure 11:
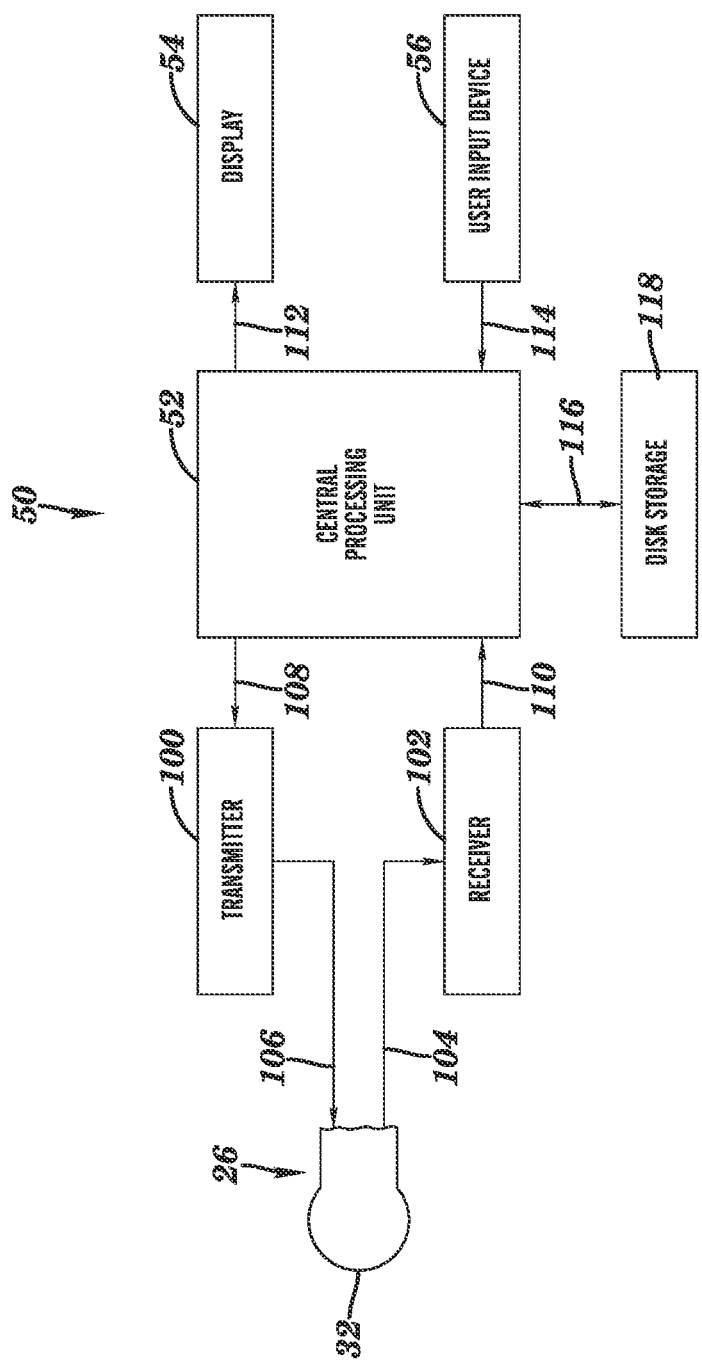
FIG. 11 is a block diagram showing the basic structure of one embodiment of an ultrasound imaging system according to the present invention.

One embodiment of the ultrasound system of the present invention is illustrated in FIG. 11. As illustrated, ultrasound imaging system 50 includes central processing unit 52, transmitter 100, receiver 102, disk storage 118, user input device 56, display 54, and transducer 32 connected to probe head 26. Central processing unit 52 is connected to transmitter 100 via electrical connector 108, which connects to probe head 26 and transducer 32 via connector 106. Connector 104 connects receiver 102 to transducer 32 and connector 110 connects receiver 102 to central processing unit 52. Connector 116 connects disk storage 118 to central processing unit 52. Display 54 is connected to central processing unit 52 via connector 112 and user input device 56 is connected to central processing unit 52 via connector 114.

Central processing unit 52 of ultrasound imaging system 50 is basically a computer that contains a microprocessor, memory, amplifiers, and power supplies for the microprocessor and for probe head 26 connected to ultrasound imaging system 50. Central processing unit 52 sends electrical currents to probe head 26 via connector 108, transmitter 100, and connector 106 to emit sound waves (via transducer 32), and also receives electrical pulses that are created from returning echoes from probe head 26 via connector 104, receiver 102, and connector 110. To generate a transmitted beam of ultrasound energy, central processing unit 52 sends command data to transmitter 100 to generate and transmit parameters to create beams of desired shape originating from a certain point at the surface of transducer 32. Transmitter 100 uses the transmit parameters to properly encode transmit signals to be sent to probe head 26. The transmit signals excite the transducer elements of transducer 32 to emit ultrasound waves.

Probe head 26 also receives backscattered waves at different times, depending on the distance into the tissue they return from and the angle with respect to the surface of probe head 26 at which they return. The received electrical signals are routed through receiver 102 to central processing unit 52. Central processing unit 52 is responsible for the calculations involved in processing the data. Once the raw data are processed, central processing unit 52 forms the image on display 54. Central processing unit 52 can also store the processed data and/or image on disk storage 118. The disks can be hard disk drives, digital video discs (DVDs), or USB flash memory drives. Typically, a patient's ultrasound scans are stored on a disk and archived with the patient's medical records.

User input device 56 is operably connected to central processing unit 52 and provides the means whereby the amplitude, frequency, and/or duration of pulses emitted from probe head 32 may be controlled. User input device 56 may also include controls whereby images displayed on display 54 are manipulated. The user input device may also have controllers that allow the clinician to adjust the sector scanning width (i.e., the width of the field of view on the image) for better imaging when e.g., going from a wide field of view to a narrower field of view. Such a feature would help to improve image quality when transitioning from e.g., a transvaginal/pelvic or procedural application that requires a wide field of view to a pediatric-related application that requires a more narrow field of view by reducing the amount of image splay.

Figure 12:
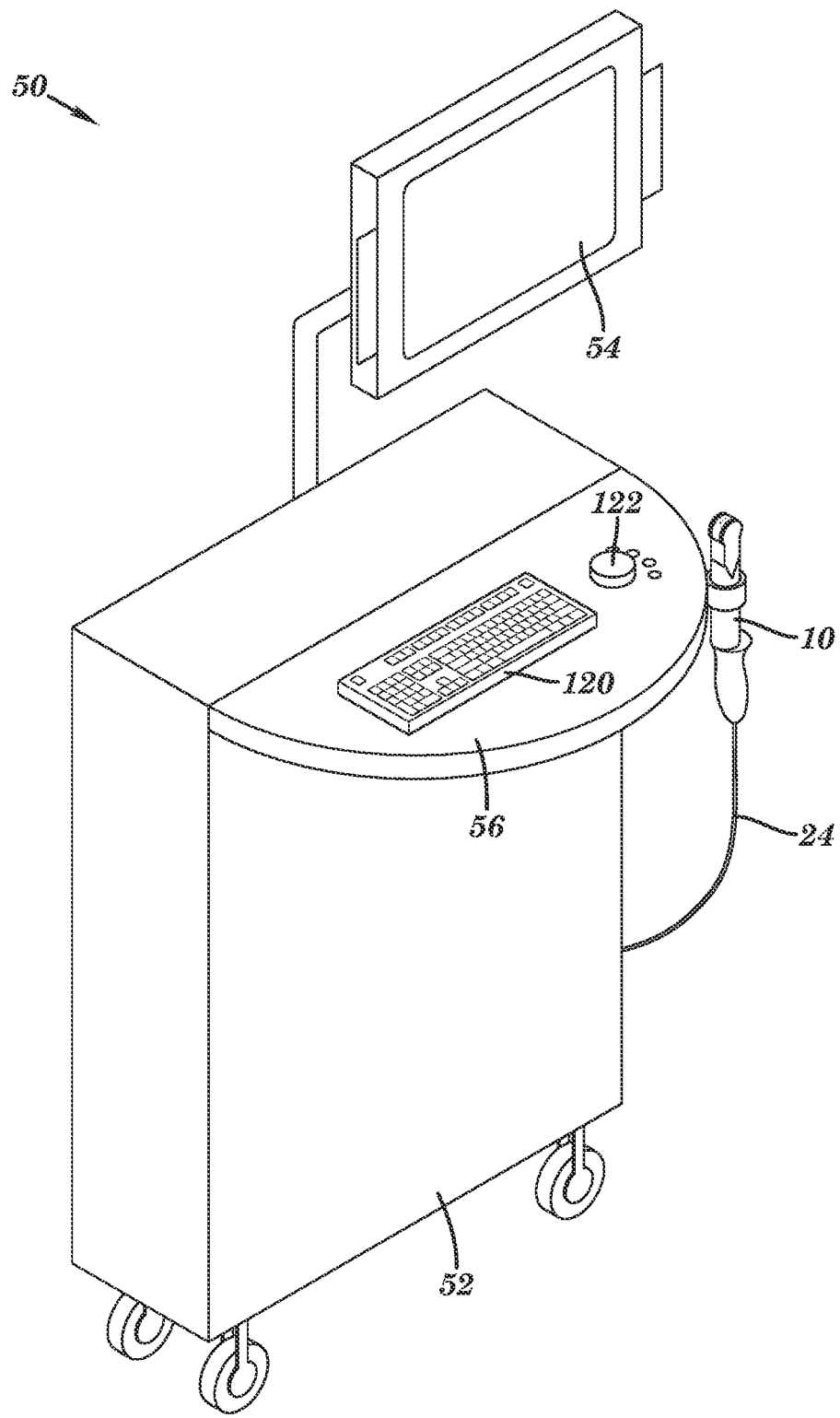
FIG. 12 is a perspective view of one embodiment of an ultrasound imaging system of the present invention. The ultrasound imaging system includes a central processing unit and a display operably connected to the central processing unit, where the display shows processed data from the central processing unit. The ultrasound imaging system also includes an ultrasonic probe device according to the present invention where the ultrasonic probe device is operably connected to the central processing unit by an electrical connector to send and receive sound waves to/from the central processing unit.

FIG. 12 illustrates one embodiment of an ultrasound imaging system of the present invention as it may be typically designed for use in a medical setting. Ultrasound imaging system 50 includes central processing unit 52 and display 54 operably connected to central processing unit 52. Display 54 shows processed data from central processing unit 52. As illustrated in FIG. 12, display 54 is a computer monitor that shows the processed data from central processing unit 52. Suitable displays can be black-and-white or color. Ultrasound imaging system 50 also includes probe device 10 according to the present invention. Probe device 10 is operably connected to central processing unit 52 via cord 24. As is typical in ultrasound imaging systems, the ultrasound imaging system of the present invention may include more than one probe device operably connected to the central processing unit.

Ultrasound imaging system 50 illustrated in FIG. 12 is also shown to include user input device 56. User input device 56 enables a clinician to set and change the frequency and duration of the ultrasound pulses as well as the scan mode of the system. As illustrated, user input device 56 may include keyboard 120 and a cursor, such as trackball 122, as commonly used with ultrasound machines, to permit a clinician to add notes to and take measurements from the data.

The ultrasound imaging system of the present invention may also include a printer that can be used to capture a hard copy of the image from the display.

In operation, the ultrasonic probe device and ultrasound system of the present invention are used to generate ultrasonic images. Accordingly, a further aspect of the present invention is directed to a method of generating an ultrasonic image. This method involves providing an ultrasound imaging system according to the present invention (which includes an ultrasonic probe device of the present invention) and inserting the probe head of the ultrasonic probe device into a subject or scanning the surface of a subject's body with the probe head under conditions effective to generate an ultrasonic image.

Suitable subjects for which ultrasonic images are generated typically include humans for diagnostic and medical imaging, but also animals in veterinary applications.

Methods of generating an ultrasonic image may be carried out by either inserting the probe head of an ultrasonic probe device of the present invention into a subject or scanning the surface (e.g., skin) of a subject's body. The advantage of the ultrasonic probe device of the present invention over other ultrasonic probe devices is that the probe device of the present invention is adaptive to either intracavitary imaging or surface scanning.

Specifically, when it is desirable to obtain ultrasonic images by an intracavitary means, it may be desirable to have the probe head attached (i.e., directly adjacent) to the elongated body. Thus, referring to FIG. 3, ultrasonic probe device 10 is shown with probe head 26 detachably connected (i.e., directly adjacent) to elongated body 12. In this configuration, ultrasonic probe 10 is suitable for transvaginal, trans-rectal, or intra-oral (intracavitary) probe head 26 insertion into a subject for ultrasonic imaging purposes.

Intracavitary insertion may include transvaginal, intra-oral, or transrectal insertion. According to this embodiment of the method of the present invention, probe head 26 transmits ultrasound beams toward the e.g., intrapelvic organs and receives the ultrasound beams reflected from them. As a result, the intrapelvic organs are sector-scanned with the ultrasound beams, and an ultrasonic tomographic image thus obtained can be displayed on a monitor using an ultrasonic imaging system of the present invention.

Alternatively, when it is desirable to scan the surface of a subject's body with an ultrasonic probe to obtain an ultrasonic image, the ultrasonic probe device of the present invention may be configured similar to that illustrated in FIG. 5, where probe head 26 is detached from elongated body 12. (It may be desirable to have much more separation between probe head 26 and elongated body 12 than what is shown in FIG. 5.) Detachment of elongated body 12 from probe head 26 (e.g., by sliding elongated body 12 along cord 24 away from probe head 26) will permit maximum movement and flexibility of probe head 26, which is particularly suitable for ultrasonic imaging in, e.g., pediatric/neonatal applications and procedural guidance where elongated body 12 is not needed and would limit movement and flexibility of probe head 26. In addition, since elongated body 12 remains connected to cord 24, the ultrasonic probe device of the present invention helps to prevent theft and/or misplacement of elongated body 12.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A two-in-one ultrasonic probe device comprising:
    an elongated body comprising a shaft portion and a handle portion, the shaft portion and handle portion being joined together to form the elongated body, the elongated body having a proximal end and a distal end, wherein the distal end comprises a first coupling and the body comprises a channel that extends from the proximal end to the distal end;
    a power cord passing through the channel, wherein the power cord is extendable and retractable relative to the distal end and proximal end of the elongated body; and
    an ultrasonic probe head connected to the power cord, wherein the power cord is capable of delivering power to the probe head, the probe head comprising a proximal end adjacent the distal end of the elongated body, wherein the proximal end of the probe head comprises a second coupling that mates with the first coupling to prevent the elongated body from rotating relative to the ultrasonic probe head, and wherein the second coupling is detachable from the first coupling, wherein when the first coupling and the second coupling are mated the elongated body and the ultrasonic probe head constitute a transvaginal probe device, and when the first coupling and the second coupling are detached, the ultrasonic probe head, independent of the elongated body, constitutes a surface scanning ultrasonic probe device suitable for pediatric applications.

2. The ultrasonic device according to claim 1, wherein when mated the first coupling and the second coupling comprise a locking joint to secure the probe head to the elongated body at the distal end of the elongated body.

3. The ultrasonic device according to claim 2, wherein the locking joint is a magnetic lock, a Luer Lock, a twist lock, a screw lock, or a releasable grip lock.

4. The ultrasonic device according to claim 1, wherein the probe head comprises a transducer element.

5. The ultrasonic device according to claim 1, wherein the probe head comprises a convex surface.

6. An ultrasound imaging system comprising:
    a central processing unit;
    a display operably connected to the central processing unit, wherein the display shows processed data from the central processing unit; and
    an ultrasonic probe device according to claim 1, wherein the ultrasonic probe device is operably connected to the central processing unit by said cord to send and receive sound waves to/from the central processing unit.

7. The ultrasound imaging system according to claim 6, wherein the probe head comprises a transducer element.

8. The ultrasound imaging system according to claim 7 further comprising:
    a user input device to change the amplitude, frequency, and/or duration of pulses emitted from the transducer element.

9. The ultrasound imaging system according to claim 6 further comprising:
    a disk storage device to store images generated by the central processing unit.

10. A method of generating an ultrasonic image, said method comprising:
    providing an ultrasound imaging system according to claim 6 and
    inserting the probe head into a subject or scanning a subject's body surface with the probe head under conditions effective to generate an ultrasonic image.

11. The method according to claim 10, wherein the subject is a human subject.

12. The method according to claim 10, wherein the probe head is inserted into a subject.

13. The method according to claim 12, wherein said inserting is carried out intracavitarily with the probe head connected to the elongated body.

14. The method according to claim 12, wherein said insertion is transvaginal, intra-oral, or transrectal.

15. The method according to claim 10, wherein the subject's body surface is scanned with the probe head.

16. The method according to claim 15, wherein said scanning is carried out with the probe head being detached from the elongated body.

* * * * *